US00PP09065P

United States Patent [19]

Evers

[11] Patent Number: Plant 9,065

[45] Date of Patent: Feb. 28, 1995

[54] HYBRID TEA ROSE PLANT NAMED TANILYKS

[75] Inventor: Hans Evers, Uetersen, Germany

[73] Assignee: Bear Creek Gardens, Inc., Medford, Oreg.

[21] Appl. No.: 268,837

[22] Filed: Jun. 29, 1994

[51] Int. Cl.[6] ..... A01H 5/00

[52] U.S. Cl. ..... Plt./15

[58] Field of Search ..... Plt. 15

*Primary Examiner*—Howard J. Locker

*Attorney, Agent, or Firm*—Klarquist Sparkman Campbell Leigh & Whinston

[57] ABSTRACT

A hybrid tea rose plant having an attractive yellow flower color; long, straight stems; vigorous, upright growth; long vase life; thick, leathery petals, and a moderate fragrance.

1 Drawing Sheet

The present invention relates to a new and distinct variety of rose plant of the hybrid tea class which was originated by me by crossing two unnamed seedlings.

The primary objective of this breeding was to produce a new rose variety having the yellow flower color and good vase life of the female parent combined with the long stems and large yellow flowers of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright growth;
2. Long (22 to 30 inches), strong, straight stems;
3. Attractive light-yellow color;
4. Long vase life;
5. Thick, round petals; and
6. Moderate fragrance.

Asexual reproduction of this new variety by budding, as performed at Uetersen, Germany, and at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—An unnamed seedling.

*Pollen parent.*—An unnamed seedling.

Classification:

*Botanical.*—Rosa hybrida.

*Commercial.*—Hybrid tea.

FLOWER

Observations made from specimens grown in a greenhouse environment at Uetersen, Germany, and Somis, Calif., from October, 1993, through March, 1994.

Blooming habit: Continuous.

Bud:

*Size.*—$1\frac{3}{4}$ inches long when the petals start to unfurl.

*Form.*—The bud form is long, pointed ovoid.

*Color.*—When sepals first divide, bud color is Yellow Group 8B. When half blown, the upper sides of the petals are Yellow Group 8B, fading to Yellow Group 8C on the outer petals; and the lower sides of the petals are Yellow Group 8B.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 137D. Shape: Funnel. Size: Broad ($\frac{1}{4}$ inch long$\times\frac{3}{8}$ inch wide). Surface: Smooth.

*Peduncle.*—Length: Short (2 to $2\frac{1}{2}$ inches). Surface: Smooth, with occasional fine hairs. Color: Medium green. Strength: Stiff, heavy.

Bloom:

*Size.*—Medium. Average open size is 4 inches.

*Borne.*—Singly.

*Stems.*—Long (average length is about 22 to 30 inches), strong.

*Form.*—When first open: High centered. Permanence: Flattens, outer petals curl back, quill fashion.

*Petalage.*—Number of petals under normal conditions: 30.

*Color.*—The upper side of the petals is Yellow Group 8B with fading to Yellow Group 8C on outer petals. The reverse side of the petals is Yellow Group 8C. The base of each petal is Yellow Group 8A. The major color on the upper side is Yellow Group 8B.

*Variegations.*—None.

*Discoloration.*—The general tonality at the end of the first day: No change. At the end of the third day: General fading on outer petals.

*Fragrance.*—Moderate.

Petals:

*Texture.*—Thick, leathery.

*Shape.*—Round.

*Form.*—Tips slightly recurved, moderately quilled.

*Arrangement.*—Imbricated, with a few small petaloids in the center.

*Persistence.*—Drop off cleanly.

*Lastingness.*—On the plant: Long (8 to 10 days). As a cut flower: Long (10 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Greenish white at the base and up two-thirds of the style. The top one-third of the style is red.

*Stigmas.*—Color: Greenish white.

Form: Bush.

Growth: Vigorous; upright; branching. As a greenhouse grown cut rose plant, height at one year (maturity) is between 5 and 6 feet with a width of 3 to $3\frac{1}{2}$ feet.

Foliage: Number of leaflets on normal mid-stem leaves:

*Size.*—Large (6 inches long$\times 4\frac{1}{2}$ inches wide).

*Quantity.*—Abundant.

*Color.*—New foliage: Underside: Grey-Orange Group 176C; Upperside: Yellow-Green Group 146B in the center of the leaf and Greyed-Orange 176C elsewhere. Old foliage: Underside: Green Group 138B; Upperside: Green Group 137A.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth, with usually 3 small, hooked, green prickles.

*Stipules.*—Medium ($\frac{1}{2}$ inch long), serrated, bearded.

*Disease resistance.*—Susceptible to mildew under normal growing conditions in a greenhouse at Somis, California.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium ($\frac{3}{8}$ inch long), hooked slightly downward.

*Color when young.*—Red.

Small pricles:

*Quantity.*—On main stalks: None. On laterals: None.

I claim:

1. A new and distinct variety of rose plant of the hybrid tea class, substantially as herein shown and described, characterized particularly as to novelty by the unique combination of its attractive yellow flower color; long, straight stems; vigorous, upright growth; long vase life; thick, round petals, and moderate fragrance.

* * * * *

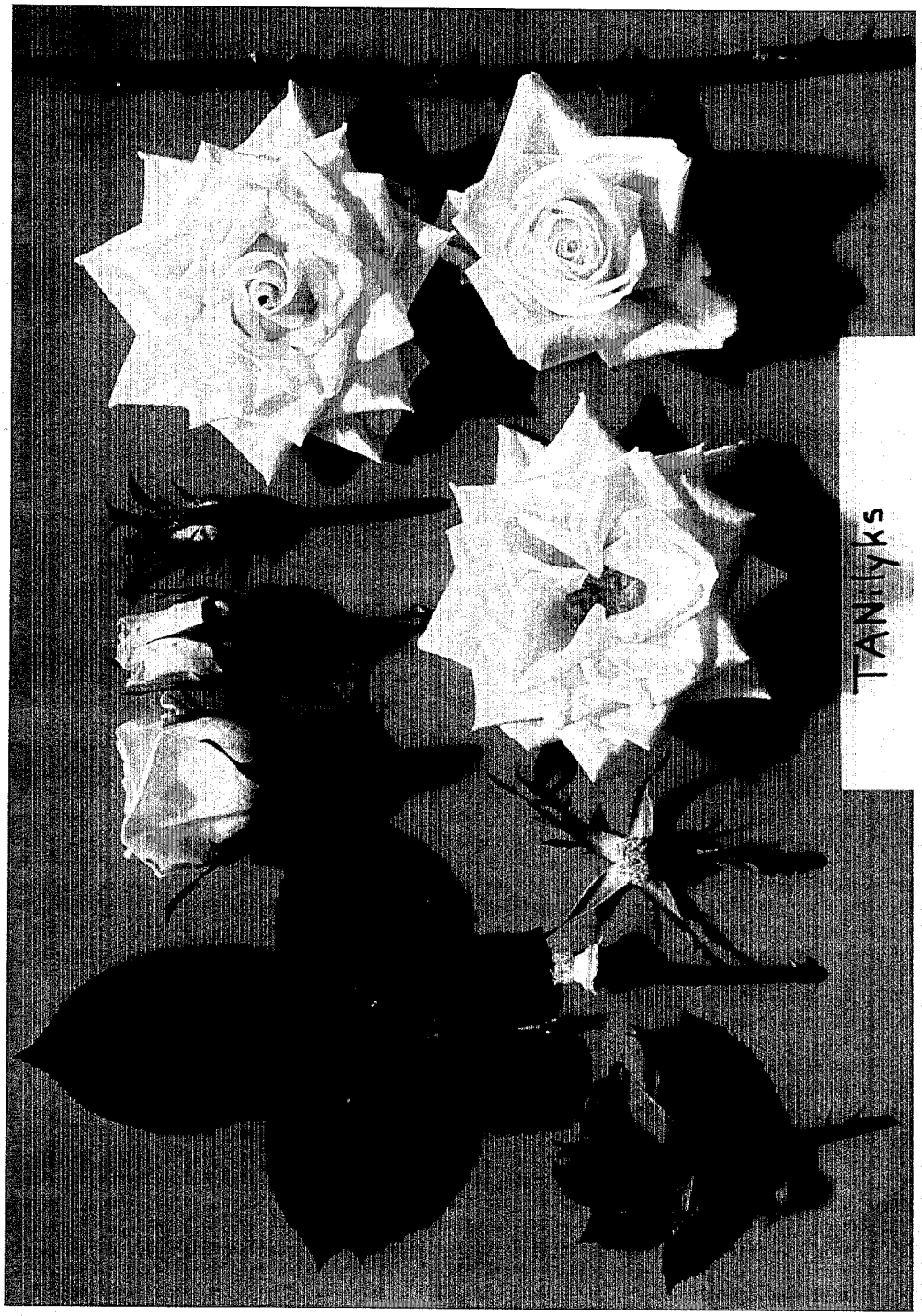
TANIlyks